United States Patent [19]

Dribbon

[11] Patent Number: 5,678,566
[45] Date of Patent: Oct. 21, 1997

[54] METHOD AND APPARATUS OF THERMOGRAPHIC EVALUATION OF THE PLANTAR SURFACE OF FEET

[75] Inventor: Bruce S. Dribbon, Wellington, Fla.

[73] Assignee: Diagnostic Thermographics, Inc., Wellington, Fla.

[21] Appl. No.: 527,529

[22] Filed: Sep. 13, 1995

[51] Int. Cl.⁶ .................................................. A61B 5/103
[52] U.S. Cl. .......................... 128/779; 128/736; 128/774
[58] Field of Search ................................. 128/774, 779, 128/736

[56] References Cited

U.S. PATENT DOCUMENTS

| 3,730,169 | 5/1973 | Fiber | 128/2 S |
| 3,830,224 | 8/1974 | Vanzetti et al. | 128/2 H |
| 3,847,139 | 11/1974 | Flam | 128/2 H |
| 4,148,951 | 4/1979 | Clark, III | 428/1 |
| 4,327,742 | 5/1982 | Meyers et al. | 128/736 |
| 4,327,743 | 5/1982 | Katz | 128/736 |
| 4,534,365 | 8/1985 | Bonetta et al. | 128/779 |
| 4,876,758 | 10/1989 | Rolloff et al. | 12/142 N |
| 4,905,383 | 3/1990 | Beckett et al. | 36/28 |
| 4,993,429 | 2/1991 | Krinsky | 128/779 |
| 5,237,520 | 8/1993 | White | 364/560 |
| 5,323,650 | 6/1994 | Fullen et al. | 73/172 |
| 5,359,791 | 11/1994 | Prahl et al. | 36/145 |

FOREIGN PATENT DOCUMENTS

4308945-A1 11/1993 Germany.
5-23307 2/1993 Japan.
WO 94/01041 1/1994 WIPO.

OTHER PUBLICATIONS

Stess et al.: "Use of Liquid Crystal Thermography in the Evaluation of the Diabetic Foot," Diabetes Care, 9(3):267–272 (May–Jun. 1986).

Benbow et al.: "The Prediction of Diabetic Neuropathic Plantar Foot Ulceration by Liquid Crystal Contact Thermography," Diabetes Care, 17(8):835–839 (Aug. 1994).

Parsley: The Hallcrest Handbook of Thermochromic Liquid Crystal Technology, pp. 1–36 (1990–1991).

*Primary Examiner*—Max Hindenburg
*Assistant Examiner*—Pamela Wingood
*Attorney, Agent, or Firm*—Holland & Knight LLP

[57] ABSTRACT

A method and apparatus for the diagnosis of abnormalities in the plantar surface of the foot employs an insole fabricated of a bottom layer of cushioning material, such as open or closed-cell foam, and a top, foot-engaging layer including a film embedded with thermochromic liquid crystals. The insoles are sized for a particular patient and inserted within his or her article of footwear. The patient then steps bare foot into the shoe and ambulates with the plantar surface of the foot in contact with the foot-engaging layer of film of the insoles for a sufficient period of time to obtain a thermographic reading on the top surface of the insole. The patient's feet are removed from the shoes, and the insoles themselves are then removed for examination and photographing of the pattern of infrared emissions produced.

8 Claims, 1 Drawing Sheet

METHOD AND APPARATUS OF THERMOGRAPHIC EVALUATION OF THE PLANTAR SURFACE OF FEET

FIELD OF THE INVENTION

This invention relates to a method and apparatus for thermographic evaluation, and, more particularly, to a method and apparatus for assisting in the diagnosis of foot disorders such as ulceration and infection on the plantar surface of the feet of a diabetic or insensate foot patient, arthritis, and, soft tissue disorders such as tendinitis, fasciitis, peripheral neuritis and interdigital neuromas.

BACKGROUND OF THE INVENTION

Thermography has been recognized as a valuable diagnostic tool for a number of conditions which elude detection by x-ray films, electromyograms and other tests. X-rays, for example, provides a visual representation of structural abnormalities, such as misalignment, subluxation and fractures. The thermograph provides the physician with a view of the physiology of the affected area, instead of its structure.

All parts of the body emit infrared heat waves produced by microcirculation of blood in the superficial tissues. Thermography is the study of the patterns of infrared heat waves which produce a "map" or pattern depending upon the heat emissions from a particular area of the body. There are generally two types of devices used to produce a thermogram, e.g., electronic and contact. Devices employing electronic thermography resemble a closed circuit television, except that instead of a photographic image, a pattern of invisible heat from the body is recorded in black and white or in a range of colors. Electronic systems generally consist of two separate units, namely, a heat camera and picture display. The camera converts the body's infrared heat emission patterns into electronic signals that are depicted on the display, typically in the form of an array of colors depending upon the relative temperature of the heat emissions from the portion of the body being examined. Photographs can be taken of the visual display to provide a permanent patient record.

Contact thermography is non-electronic and employs thermochromic liquid crystal technology to obtain a visual pattern of infrared heat emissions from a particular area of the body. U.S. Pat. No. 4,327,742 to Meyers et al., for example, discloses an apparatus comprising an inflatable chamber formed with opposed first and second walls. The first wall includes an elastic sheet embedded with temperature responsive liquid crystals, and the second wall is a sheet of transparent material, such as glass or lexane. Air is introduced into the chamber formed by the opposed sheets so that the flexible elastic sheet, when in an inflated state, can assume a convex shape and conform to various highly contoured portions of the body. Another contact thermography system is disclosed in U.S. Pat. No. 4,327,743 to Katz. The Katz device employs a first elastic film containing temperature responsive liquid crystals which is positioned immediately adjacent a second elastic film having a different modulus of elasticity. The two sheets or films are attached to one another solely along their periphery to provide an air space therebetween. A different pressure is created between the two layers, either by inflation or by drawing a vacuum, so that any air between the two films is forced out along the edges thereof permitting the films to stretch and independently conform to essentially any complex tissue shape so that an accurate thermographic reading can be obtained for that tissue.

One area in which thermography has been identified as a potential diagnostic tool is in the treatment of the diabetic and insensate foot patient. Unable to feel pain, the insensate foot patient is at great risk of foreign body infiltration, shoe irritation and the trauma caused by simple ambulation. It has been found that typically only after blood appears on the sock or shoes will such a patient seek treatment, but by that time serious damage may have already occurred. Research has been conducted with respect to the effectiveness of contact thermography as a diagnostic tool to detect areas of tissue damage and inflammation which can lead to ulceration on the plantar surface of the foot. See Stess et al.: "Use of Liquid Crystal Thermography in the Evaluation of the Diabetic Foot," *Diabetes Care.*, 9(3):267–272 (May–June, 1986); Benbow et al.: "The Prediction of Diabetic Neuropathic Plantar Foot Ulceration by Liquid-Crystal Contact Thermography," *Diabetes Care*, 17(8)835–639 (August, 1994); and Dribbon: "Thermography and Diagnosis," *Pain Practitioner, the Quarterly Newsletter*, pp. 3–4. As explained in these articles, tests indicate that contact thermography is a viable diagnostic tool which is capable of providing an indication of abnormalities in the diabetic foot even before the occurrence of ulceration or other tissue damage.

Unfortunately, the diagnoses obtained in connection with the studies documented in the above-identified publications all rely upon equipment of the type disclosed in U.S. Pat. Nos. 4,327,742 and 4,327,743. In conducting a thermographic examination with such equipment, the patient places his or her bare feet onto an elastic sheet carrying the temperature-responsive liquid crystals, usually when lying down on an examination table. This technique fails to provide a true representation of the foot's thermal pattern which actually occurs inside of the shoe, or any other article of footwear, worn by the diabetic or insensate foot patient. Footwear exerts a significant biomechanical force and control on the foot, particularly in patents who exhibit pathomechanics. In the diabetic or insensate foot patient, the ability to perceive the position of the foot in the shoe, and any irritation caused by that shoe, is severely impaired. As the insensitivity increases over the course of the disease, the patient is inclined to purchase shoes that are smaller in size so that he or she may experience some feeling of the shoe's presence on the foot. Any irritation of the tissue can go unrecognized by the patient until blood is visible on the shoe or sock. None of the shoe conditions which actually cause the irritation of the foot can be accounted for when employing contact thermographic devices, and diagnostic techniques, of the type described above.

In addition to the diagnosis of potential ulceration of the feet, thermography has been suggested for use in the diagnosis and treatment of arthritis and soft tissue disorders such as tendiuitis, fasciitis, peripheral neuritis and interdigital neuromas. See "The Use of Liquid Crystal Thermography in Diagnosis and Treatment," Dribbon. It has been observed that the identification of areas of increased heat can be beneficial to the treatment of arthritis, athletes, peripheral vascular patients, patents with benign and malignant lesions and others who exhibit such conditions as infections, fractures, malignancies and/or bursitis/capsulitis among other disorders.

Nevertheless, as with the problems of ulceration, the foregoing conditions have been diagnosed with thermographic equipment of the type disclosed in U.S. Pat. Nos. 4,327,742 and 4,327,743. While each of these conditions may be affected by the biomechanical forces and control exerted by footwear on a patient's foot, as described above, existing diagnostic methods and devices fail to account for such effects.

SUMMARY OF THE INVENTION

It is therefore among the objectives of this invention to provide a method and apparatus for the diagnosis of abnormalities in diabetic and insensate foot patients, and patients exhibiting other foot conditions, which accounts for the biomechanical forces and control exerted on the foot by particular articles of footwear worn by the patient.

These objectives are accomplished in a method of diagnosis which employs an insole fabricated of a bottom layer of cushioning material, such as open or closed-cell foam, and a top, foot-engaging layer including a film embedded with thermochromic liquid crystals. The insoles are sized for a particular patient and inserted within his or her article of footwear. The patient then steps bare foot into the shoe and ambulates with the plantar surface of the foot in contact with the foot-engaging layer of film of the insole for a sufficient period of time to obtain a thermographic pattern on the top surface of the insole. The patient's feet are removed from the shoes, and the insoles themselves are then removed for examination and photographing of the pattern of infrared emissions produced.

The insole and diagnostic method of this invention, unlike prior diagnostic methods and devices, is effective to obtain an accurate pattern or map of the infrared heat waves emitted from the plantar surface of a patient's foot within the particular article of footwear he or she normally wears. The biomechanical forces and control on the foot exerted by the shoes are reflected in the thermographic patterns obtained on the insole. These thermal patterns inside the shoe are subjected to a temperature variant, i.e., the shoe is enclosed, and, consequently, the thermal emissions from the plantar surface of the foot are evaluated within the closed environment within which the patient functions on a regular basis.

By allowing the physician and/or patient to constantly evaluate the tissue status in this manner, it is plausible to map the thermal patterns and utilize them as indicators of the tissue profusion and, therefore, viability. The patterns reflect the exertion of forces the shoe brings to the biomechanics involved. With an accurate indication of how the foot is acted on by the shoe, the physician or podiatrist is in a much better position to prescribe a preventative program of foot care which can include an accommodation of pressure areas, debridement of plantar callus, specialized orthotic or customized shoe gear, and, in the case of diabetic patients, an overall monitoring of the patient's diabetes. Such treatment is enhanced because the attending physician is provided with the means to accurately determine potential problem areas of that patient within the particular article of footwear he or she ordinarily wears, and then very accurately prescribe a particular preventative program which will take into account how the patient's foot is acted upon by such article of footwear.

DESCRIPTION OF THE DRAWINGS

The structure, operation and advantages of the presently preferred embodiment of this invention will become further apparent upon consideration of the following description, taken in conjunction with the accompanying drawings, wherein.

DESCRIPTION OF THE INVENTION

Figure 1:
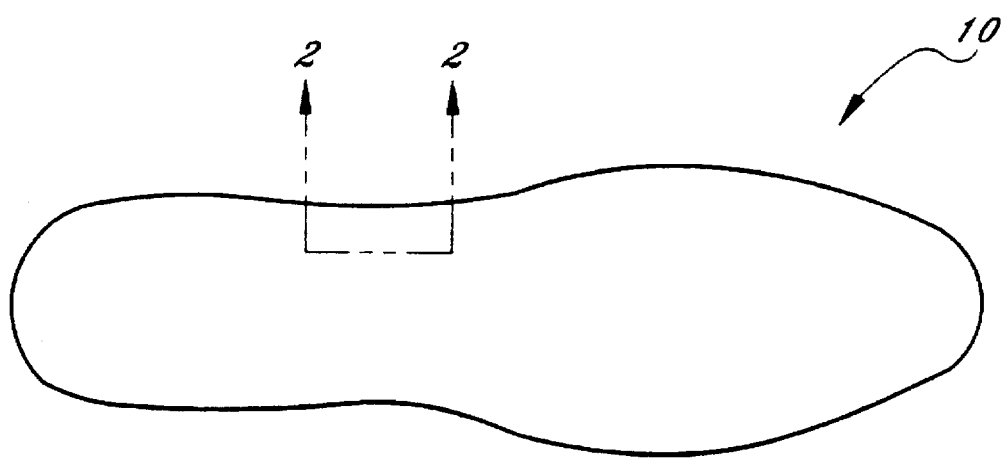
FIG. 1 is a top view of the insole of this invention.
Figure 2:
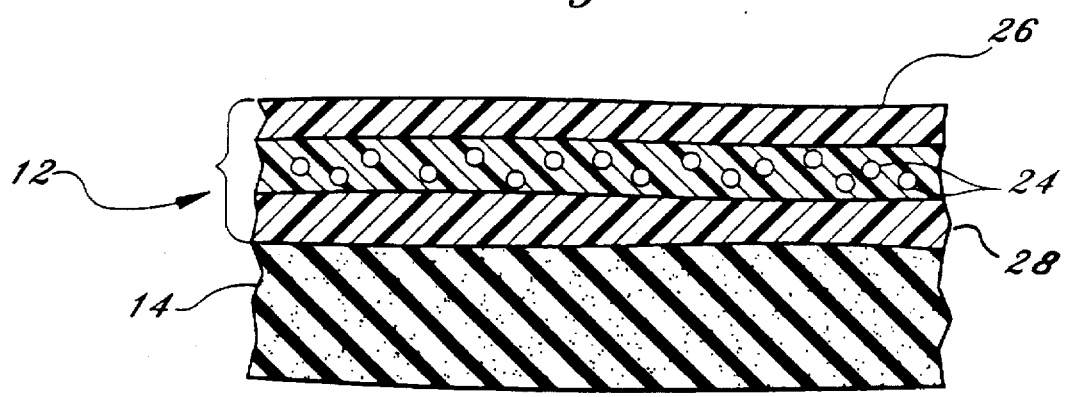
FIG. 2 is a cross-sectional view taken generally along line 2—2 of FIG. 1.
Figure 3:
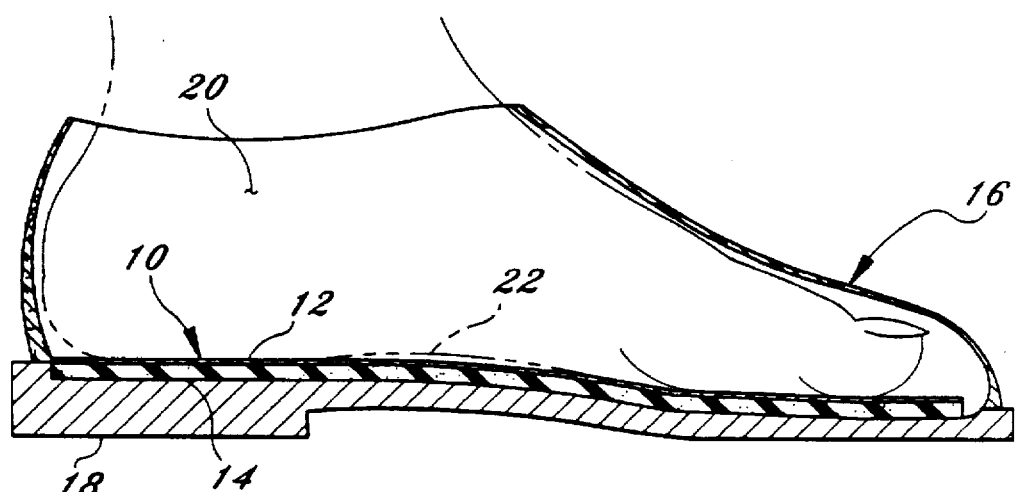
FIG. 3 is a view in partial Cross-section of the insole herein within an article of footwear and with a patient's foot atop the insole.

Referring now to the Figs., an insole 10 in accordance with this invention is schematically depicted. The insole 10 comprises a top, foot-engaging layer 12 affixed to a cushioning layer 14. The insole 10 is adapted to be placed within the interior of an article of footwear such as a shoe 16 atop the outsole 18 of the shoe. As described below, the foot 20 of a patient is inserted within the shoe 16 so that the plantar surface 22 of the foot rests atop the foot engaging layer 12 of insole 10 to provide a diagnosis of the condition of the plantar surface 22 of the foot 20.

In the presently preferred embodiment, the foot-engaging layer 12 of insole 10 comprises a thin layer of microencapsulated, thermochromic liquid crystals 24 sandwiched between a transparent polymer sheet 26 and a black absorbing background layer 28 affixed to the cushioning layer 14. The sheet material forming foot-engaging layer 12 is commercially available and the details of its construction form no part of this invention. A detailed discussion of same can be found in the publication "The Hallcrest Handbook of Thermochromic Liquid Crystal Technology" published by Hallcrest Products, Inc. of Glenview, Ill., the disclosure of which is hereby incorporated by reference in its entirety herein. For purposes of the present discussion, thermochromic liquid crystals 24 are heat-sensitive and have the property of exhibiting different colors, when visualized against a black background, indicative of the temperature of an object placed thereagainst. As described below in connection with a discussion of method of diagnosis of this invention, the thermochromic liquid crystals 24 are useful in providing an indication of the infrared thermal emissions from the plantar surface 22 of the foot 20 of a particular patient.

As noted above, the foot engaging layer 12 of the insole 10 herein is affixed to a cushioning layer 14. In the presently preferred embodiment, the cushioning layer 14 is formed from a foam material such as latex foam, cross-linked polyethylene foam, ethylene vinyl acetate foam, ethylene vinyl acetate enhanced cross-linked polyethylene foam, sponge rubber foam, vinyl sponge foam, urethane and others. Further, the cushioning layer 14 may comprise a laminate of two or more of the foams noted above, and/or other foam materials as desired.

The diagnostic method of the subject invention is particularly directed toward providing the attending physician with a visual indication of potential sites of ulceration on the plantar surface 22 of the foot 20 of diabetic patients or others with an insensate foot condition, and to assist in the detection of such conditions as arthritis, fractures, malignancies and soft tissue disorders including tendinitis, fasciitis, peripheral neuritis and interdigital neuromas. The diagnostic method herein accounts for the biomechanical forces and control exerted on the foot by the construction of a particular article of footwear, so that a treatment regimen can be prescribed for given patient in the shoes or other articles of footwear he or she normally wears.

In particular, the insole 10 of this invention is sized to fit within the interior of the shoe 16 of a particular patient. The insole 10 is inserted within the interior of the shoe 16 so that its cushioning layer 14 rests atop the outsole 18 of the shoe 16. It is contemplated that with athletic shoes, or other footwear having removable insoles, the original insole is removed and then temporarily replaced by the insole 10 of this invention. In the case of shoes where the original insole is not removable, the insole 16 herein is merely placed atop the original insole.

The patient then steps bare foot into the shoe 16 so that the plantar surface 22 of the foot 20 contacts the foot engaging layer 12 of the insole 10. Preferably, the patient is encouraged to ambulate and maintain his or her plantar surface 22 in contact with the foot engaging layer 12 of insole 10 for a sufficient period of time to create a colored, visual indication of the thermal emissions from the plantar surface of the foot 20. As described above, the thermochromic liquid crystals 24 respond to the infrared thermal emissions from the plantar surface 22 by producing a pattern of colors which can be visualized against the black absorbing layer 28 of foot engaging layer 12. Typically, a brownish-red color is produced in response to lower temperatures, green color indicates an intermediate temperature, and blue colors denote higher temperatures of thermal emission from the plantar surface 22 of foot 20. Such a color pattern or map is studied by the attending physician after the patient takes off the shoe 16 and the physician removes the insole 10 from the shoe interior. If desired, the insole 10 can be immediately photographed by the physician to provide a permanent record of the thermal emission pattern of such patient.

As described in detail in the articles mentioned above, the map or thermal emission pattern which can be visualized on the sheet material forming the foot engaging layer 12 of insole 10 is useful in the diagnosis of potential sites of ulcerization or other problems with the soft tissue of the diabetic or insensate foot patient. It has been observed that diabetic patients exhibit generally decreased temperatures on the plantar surface of their feet compared to non-diabetic patients, and "hot spots" represented by blue-colored patterns can indicate areas of tissue damage and perhaps inflammation produced by mechanical trauma. Additionally, areas of increased temperature can be indicative of infection, fracture, tendinitis, malignancy and bursitis/capsulitis among other disorders. It is believed that such hot spots are created by increased blood flow in the superficial tissues due to arteriovenous shunting around a site of possible ulceration. Because the thermal emissions of the patient's foot 20 are evaluated within the closed environment of the shoe, and in response to the exertion of biomechanical forces by the shoe, the attending physician is provided with an accurate indication of potential problem areas by the method of this invention for each individual patient within the shoes or other articles of footwear he or she normally wears. This enables the physician to prescribe special inserts, support devices, or other orthoses for use within that pair of shoes to prevent rubbing, chaffing or other contact between the foot, toes and shoe which might eventually lead to ulceration or other tissue damage. This process can be repeated for a number of shoes worn by each patient, thus enabling the physician to prescribe specific treatment regimens for each different article of footwear.

While the invention has been described to a preferred embodiment, it will be understood by those skilled in the art that various changes may be made and equivalents may be substituted for elements thereof without departing from the scope of the invention. In addition, many modifications can be made to adapt a particular situation or material to the teachings of the invention without department from the essential scope thereof.

For example, it is contemplated that the insole 10 of this invention could be formed of a footprint-shaped foot engaging layer 12 without the inclusion of a cushioning layer 14. In this embodiment, the foot-engaging layer 12 is inserted directly atop the existing insole within the interior of a particular article of footwear, and the method of diagnosis proceeds in the same manner described above.

Therefore, it is intended that the invention not be limited to the particular embodiment disclosed as the best mode contemplated for carrying out this invention, but that the invention will include all embodiments falling within the scope of the appended claims.

I claim:

1. A method of detecting abnormalities in the plantar surface of the feet, comprising:

inserting a footprint-shaped member having a thermally sensitive foot-engaging surface into an article of footwear;

inserting the bare foot of the patient into the article of footwear in contact with the thermally sensitive foot-engaging surface of the member for a sufficient period of time to permit the formation of thermal patterns on the foot engaging surface which are representative of the thermal emission patterns of the plantar surface of the foot within that article of footwear;

removing the member from the article of footwear;

performing an examination of the thermal emission patterns on the foot engaging surface of the member, conducted by the patient or a health care professional, to identify potential and existing sites of abnormalities on the plantar surface of the patient's foot.

2. The method of claim 1 in which said step of inserting the member into the article of footwear comprises inserting a footprint-shaped insole including a top layer having the foot engaging surface and a second layer formed of a cushioning material.

3. The method of claim 1 in which said step of inserting the member into the article of footwear comprises inserting a member whose foot engaging surface includes thermochromic liquid crystals.

4. A method of detecting abnormalities in the plantar surface of the feet, comprising:

inserting a footprint-shaped insole having a foot-engaging layer incorporating thermally sensitive thermochromic liquid crystals into an article of footwear;

inserting the bare foot of the patient into the article of footwear in contact with the thermally sensitive foot-engaging surface of the insole for a sufficient period of time to permit the formation of thermal patterns on the foot engaging surface which are representative of the thermal emission patterns of the plantar surface of the foot within that article of footwear;

removing the member from the article of footwear;

performing an examination of the thermal emission patterns on the foot engaging surface of the insole, conducted by the patient or a health care professional, to identify potential and existing sites of abnormalities on the plantar surface.

5. An insole for an article of footwear, comprising:

a foot-engaging layer, said foot-engaging layer including a temperature sensitive material capable of producing a visual indication of thermal emissions from the plantar surface of the foot;

a cushioning layer affixed to said foot-engaging layer, said cushioning layer being adapted to overlie the outsole of an article of footwear.

6. The insole of claim 5 in which said foot-engaging layer comprises thermochromic liquid crystals sandwiched between a transparent polymer layer and a black absorbing background layer.

7. The insole of claim 5 in which said cushioning layer is formed of foam material.

8. The insole of claim 7 in which said foam material is chosen from the group consisting of urethane foam, latex foam, cross-linked polyethylene foam, sponge rubber foam, vinyl sponge foam, ethylene-vinyl acetate foam and ethylene-vinyl acetate enhanced cross-linked polyethylene foam.

* * * * *